United States Patent

McSymytz

[11] Patent Number: 5,179,944
[45] Date of Patent: Jan. 19, 1993

[54] HOT/DRY, HOT/MOIST OR COLD THERAPY PAD

[76] Inventor: Laurie L. McSymytz, 148 Cardinal Crescent, Regina, Saskatchewan, Canada, S4S 4Y7

[21] Appl. No.: 760,525

[22] Filed: Sep. 16, 1991

Related U.S. Application Data

[63] Continuation-in-part of Ser. No. 643,477, Jan. 22, 1991, abandoned.

[51] Int. Cl.⁵ .............................................. A61F 7/00
[52] U.S. Cl. .................................... 128/403; 128/402; 62/530
[58] Field of Search .................... 128/399–403, 128/379, 380; 62/530; 383/901

[56] References Cited

U.S. PATENT DOCUMENTS

| | | | |
|---|---|---|---|
| 3,587,578 | 6/1971 | Walker | 128/402 |
| 3,815,610 | 6/1974 | Winther | 128/403 |
| 3,889,684 | 6/1975 | Lebold | 128/402 |
| 3,900,035 | 8/1975 | Welch et al. | 128/402 |
| 4,645,498 | 2/1987 | Kosak | 128/403 |
| 4,742,827 | 5/1988 | Lipton | 128/380 |
| 4,920,964 | 5/1990 | Francis | 128/403 |
| 5,016,629 | 5/1991 | Kanare | 128/402 |

FOREIGN PATENT DOCUMENTS 2742030  3/1979  Fed. Rep. of Germany ...... 128/402

Primary Examiner—Mark Graham
Attorney, Agent, or Firm—Adrian D. Battison; Stanley G. Ade; Murray E. Thrift

[57] ABSTRACT

A therapeutic pad is formed from a container having elongate compartments arranged in parallel relationship across the width of the container and extending substantially across the full length of the container. The container is formed from a fabric material which is permeable to moisture but contains the filler material which is sand. The compartments are filled with the sand. The use of sand allows moisture to be applied to the container which will then be held within the interstices of the sand for either heating by microwave or cooling by freezing. A separate cover is formed from a quilted padded fabric material shaped to double the size of the container so that it can be folded to cover both sides of the container. One half of the cover includes a moisture impermeable layer to prevent the escape of moisture from that side while the other side allows the escape of moisture. This allows the user choice of applying either moist heat or dry heat to the body of the patient.

1 Claim, 2 Drawing Sheets

HOT/DRY, HOT/MOIST OR COLD THERAPY PAD

This application is a continuation-in-part of U.S. Ser. No. 07/643,477 filed Jan. 22, 1991 now abandoned.

BACKGROUND OF THE INVENTION

The present invention relates to a pad which can be used for example for application of heat or cooling to a body part.

The application of heat or cooling is a well known therapy and despite its simplicity is highly effective in alleviating pain and providing healing of various maladies.

Various proposals for pads have been made in the patent literature and various products are currently available. One current product which is widely used for this purpose comprises a fabric cover which contains granules of a heat absorbing particulate material formed from a suitable plastics material. This product is generally heated by placing the product in boiling water which communicates the heat from the water to the plastics filling material which has a sufficiently high specific heat to retain the heat applied for significant period of time. However boiling of the product is of course inconvenient and messy and results in a product which is dripping with boiling water and accordingly is difficult to handle. In addition this product is not suitable for freezing. The application of cold therapy is generally carried out by a separate product provided by a freezer pack which is simply an impermeable plastics layer containing a freezable liquid such as water, mixture of water and alcohol or other materials. This product again is difficult to handle. In both cases the products are relatively expensive and are prone to failure.

The heating therapy pad described above is divided into pockets or compartments which are rectangular and formed by stitch lines transversely to the length of the pad and longitudinally of the pad thus defining a plurality of pockets of rows and columns.

The patent literature describes various different styles of therapy pad containing various different materials.

Canadian patent 551,460 (Jensen) discloses a pad formed by rows and columns of compartments within which is provided a relatively small amount of a water insoluable hydro-philic inorganic material possessing the ability to absorb and retain an amount of water equal to at least four times and preferably ten times its volume. One example of such a material is Bentonite which is provided in the form of a stiff paste like consistency holding large quantities of water. This product is unsatisfactory in that it is messy to handle when wet and also difficult or impossible to dry so that it cannot be maintained in a hygenic condition and needs the application of fungicide.

Canadian patent 066,953 (Cheney) discloses a similar product but in this case it uses pulverized soap stone which is similar in form to talcum powder. This product clearly states that the material cannot be moistened or wetted since any moistening or soaking with medicinal fluids would destroy the article as a warming pad. The dry powder is of course difficult to contain and will tend to escape from any porous or water permeable cover.

German application 3730039 (Leyerer) discloses a cushion for hot or cold treatment of patients which is made of a cover with a filling of a heat storage material such as granules which are contained in cubicle chambers into which the cushion has been subdivided. The preferred material for the covers is polyurethane and for the filling a two component silicone rubber with sand or metal granules. The covering is therefore not water permeable and there is no intention to wetten or moisten the filler material.

SUMMARY OF THE INVENTION

It is one object of the present invention, therefore, to provide an improved therapy pad which is simple and economic in construction and accordingly can be sold at a relatively low price and can be used to provide an effective source of heating and cooling for use either in cold therapy or in heat therapy as required.

According to the invention, therefore, there is provided a therapy pad comprising a substantially planar container having two sides, a filler material received within the container, the container being formed from a flexible fabric material which is resistant to heating and freezing, is permeable to moisture and retains the filler material within the container, the container being formed into a plurality of separate elongate parallel tubular compartments each extending substantially wholly across a width of the sides of the container and the compartments being arranged in a row from one end of the sides of the container to an opposed end of the container with each compartment being separated from a next to allow flexing of the container about a line between the compartments, the filler material consisting substantially wholly of sand.

According to an important preferred aspect of the invention, there is provided a cover for the container comprising a padded fabric body shaped to cover both sides of the container, with one side of the cover being permeable to moisture to allow the application of moist heat to the patient and the other side of the cover being impermeable to moisture to prevent penetration of the moisture to cause application of dry heat to the patient at the choice of the patient.

According to a second aspect of the invention there is provided a method of applying therapy to a patient comprising the steps of providing a therapy pad comprising a substantially planar container having two sides and a filler material received within the container, the container being formed from a flexible fabric material which is resistant to heating and freezing, is permeable to moisture and retains the filler material within the container, the container being formed into a plurality of separate elongate parallel tubular compartments each extending substantially wholly across a width of the sides of the container and the compartments being arranged in a row from one end of the container to an opposed end of the container with each compartment being separated from a next to allow flexing of the container about a line between the compartments, the filler material consisting substantially wholly of sand, applying water to the pad to wetten the sand, applying one of heating and cooling to the container and filler to cause heating and freezing respectively of the water retained within the sand, placing the container within a cover formed of a padded fabric body so that the body covers both of said sides of the container and applying the cover body to the patient.

Although the main purpose of the invention relates to hot or cold therapy, the same device may be used for many other purposes including:

a) a weight for use in exercise;

b) a warmer for cold hands or feet;

c) a support when rolled contours form support for the body for example as a neck roll;

d) an insulator for keeping food and drinks hot or cold;

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
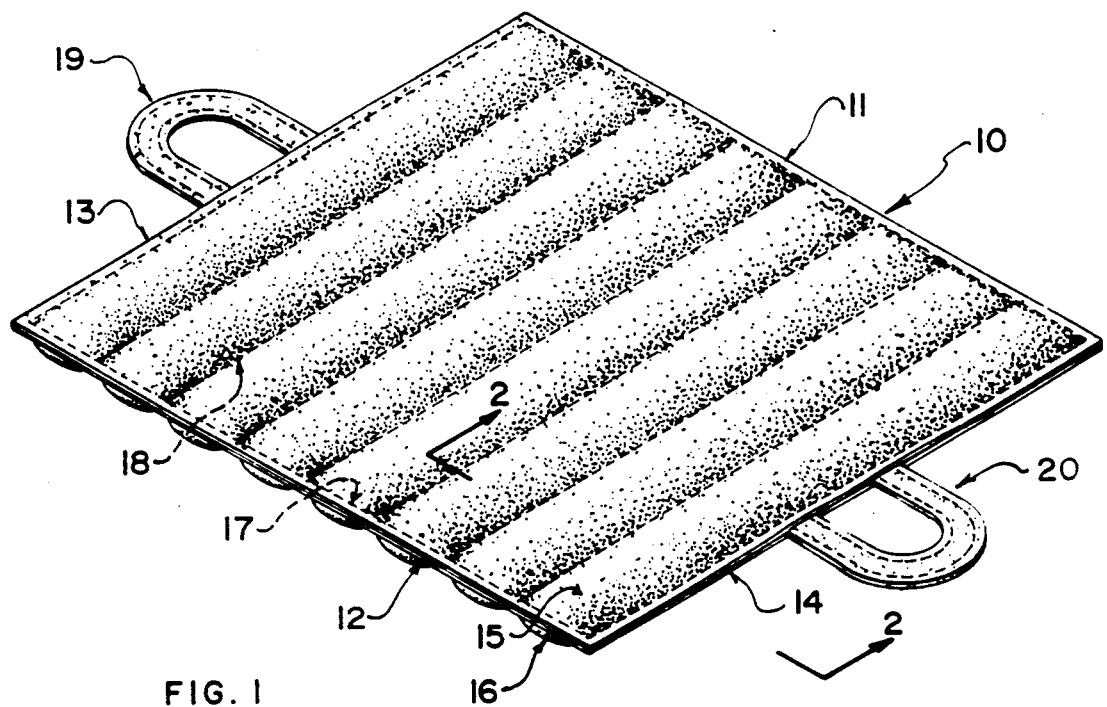
FIG. 1 is an isometric view of an inner container portion of a therapeutic pad according to the present invention.

The therapy pad according to the present invention comprises a rectangular body 10 having two parallel sides 11 and 12 and two parallel ends 13 and 14 generally at right angles to the sides. The body is formed from two overlying layers of fabric 15 and 16. The layers are stitched together around the outside edges by stitch lines indicated as dash lines 17. In addition there are stitch lines 18 extending transversely across the layers with the stitch lines 18 lying parallel to the ends 13 and 14 so as to form the layers into a plurality of tubular pockets with each pocket extending across the full width of the pad. In practice each pocket has a width of the order of half to one inch and length of the full width of the pad. A pair of handles 19 and 20 are formed from the same fabric and are stitched into the end stitch line so as to hold the handles in position as structurally part of the pad.

Before the final end stitch line is applied, each pocket is filled with sand. The fabric is formed from a suitable water permeable woven material for example a cotton fabric which is sufficiently fine mesh to maintain the relatively course granules of the sand fully confined within the material without possibility of escape. The pockets are filled to substantially the maximum extent consistent with completing the final finish line of stitches to close the pockets thus maintaining them permanently and fully closed.

In use the pad is firstly immersed in water 25 which can be simply cold water without any heating applied. The water permeability of the fabric covering ensures that the water fully permeates into the pockets and fills the interstices between the sand granules. The sand however remains substantially unaffected by the water and does not significantly mix with the water to form any kind of paste or other emulsion which is difficult to dry. However the sand has sufficient interstices to carry a significant quantity of water as the pad is removed from the water. The pad can then either be heated in a microwave oven 26 or can be frozen in a freezer 27. In the freezing situation, the pad is simply placed into the refrigerator and frozen until the water retained within the interstices in the sand is turned to ice thus forming the device into substantially a row of solid elongate bodies defined by the pockets and the contained sand and ice.

The use of sand is particularly effective in the pad in that it is very inexpensive, can retain significant quantities of water without mixing or emulsifying with the water. The sand furthermore does not swell and hence there are no problems with increasing or decreasing of the size of the pockets. The sand can be readily dried after use so that there is little or no difficulty with development of organisms within the product thus enabling it to be maintained sterile without difficulty.

The shape of the pockets is selected so that the device remains flexible even when the filler material is frozen solid. The product can therefore be wrapped around or applied to a specific area of the body of the user without difficulty and following relatively closely the shape of various regions of the body.

The sand cooperates with the moisture permeable material so that the sand does not in any way escape to cause formation of dust or other undesirable pollutants. At the same time the fabric can be readily moisture permeable to allow rapid take up of water when the product is immersed to avoid delays. The sand and the fabric are resistant to microwave heating so that the product can be heated very rapidly and used immediately without delay and without the mess and inconvenience of other boiling techniques. The positioning of the handles at the ends of the device enable the product to be lifted simply while it remains structurally sound due to the pockets being retained substantially rigid by their substantially complete filling with the sand.

Figure 2:
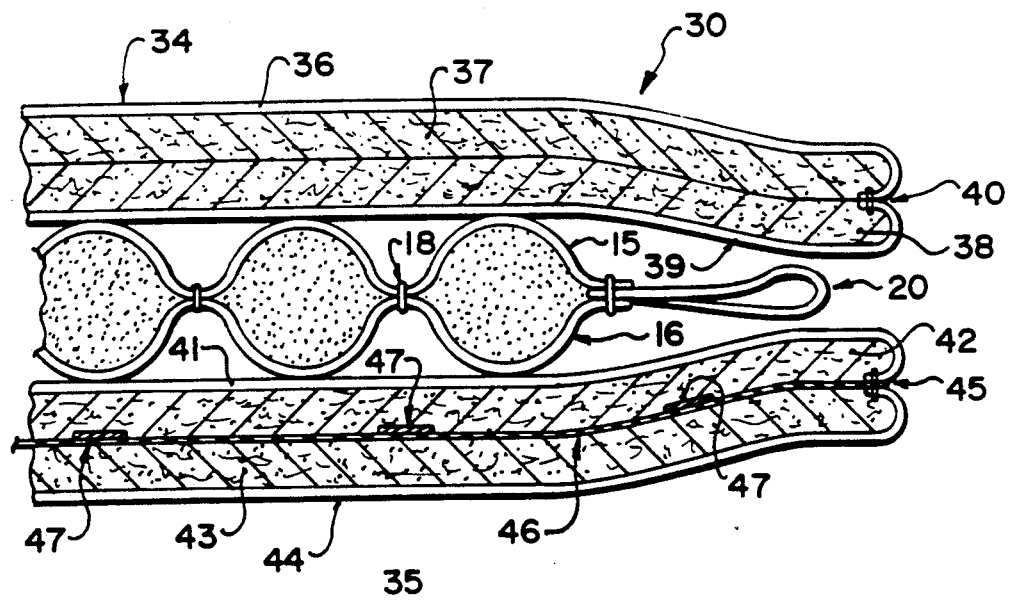
FIG. 2 is a cross-sectional view along the lines 2—2 of FIG. 1 also showing an outer cover portion.
Figure 3:
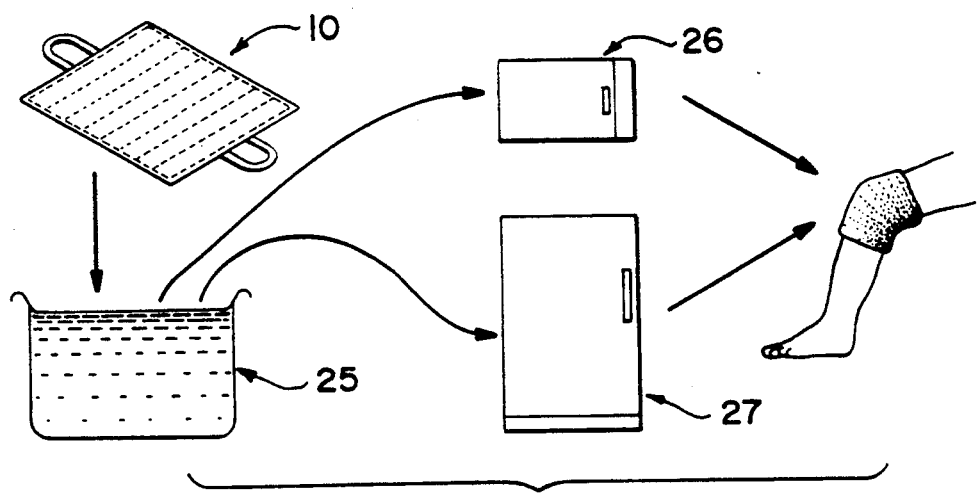
FIG. 3 is a schematic illustration of the system of use of the therapeutic pad according to the present invention.
Figure 4:
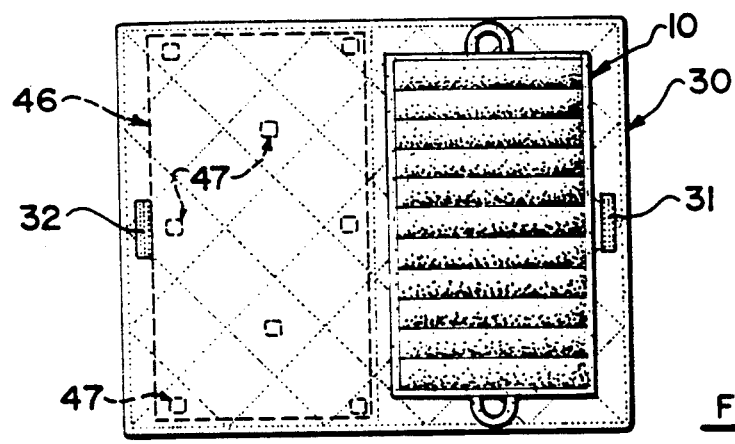
FIG. 4 is a plan view of the container portion and cover portion in an open condition.

Turning now to FIGS. 2 and 4, the second part of the therapy pad is shown which comprises a cover 30 within which the container portion including the sand is received. The cover 30 comprises a substantially rectangular layer of a padded fabric material. In plan view the pad has a dimension substantially double that of the container so that in opened condition it can lie flat with the container received on one half of the cover and then the cover can be folded along a center line to fully enclose the container with the cover being closed by a suitable fastening mechanism 31 and 32 which may be of the hook and loop type.

The cover is formed from two layers of a quilted padded fabric material as best shown in FIG. 2. In FIG. 2 the container is shown enclosed by a top side 34 of the cover and a lower side 35 of the cover. The top side 34 is formed from two layers of the padded fabric material which comprises a layer 36 of fabric and a layer 37 of a padding material such as a foam or loose mesh nonwoven material. The top side 34 further includes a second layer of the padding indicated at 38 and a second layer of the fabric 39. The fabric is stitched along a stitch line 40 to close the fabric structure. The lower side 35 is similarly formed from an inner fabric layer 41, an inner padding layer 42, an outer padding layer 43 and an outer fabric layer 44. A stitch line 45 closes the structure. In addition a moisture impermeable layer 46 is added between the two padding layers 42 and 43. This moisture impermeable layer 46 preferably of polyethylene or a similar suitable flexible plastics material is held in place by pads of an adhesive 47 applied to one of the padding layers 42 and 43 prior to assembly of the two layers enclosing of the stitched line. Each of the layers defined by one of the fabric layers and one of the padded layers is quilted in conventional manner to provide an effective structure for the cover.

As shown in FIG. 4, the layer 46 substantially fills one half of the cover from the closed position it fully overlies the shape of the container. Thus when the container is heated as previously described, it is carried carefully by the user using the handles and placed onto the opened cover structure. The cover is then closed to enclose the heated pad to prevent burning of the skin by accidental contact directly with the container itself.

The presence of the moisture impermeable layer 46 on one half only of the cover allows the user to select either the application to the skin of heat with moisture or dry heat depending upon which surface of the cover is applied to the body.

Figure 5:
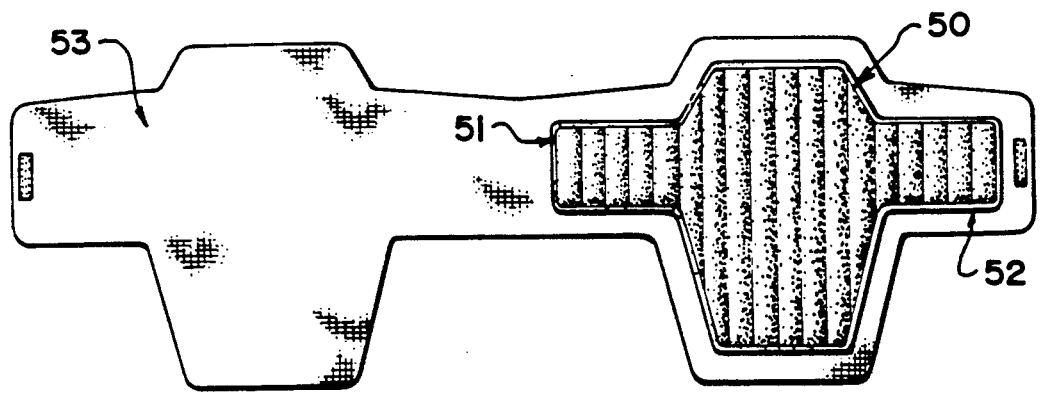
FIG. 5 is a plan view of a second embodiment of the pad.

Turning now to FIG. 5, a modified shape of the structure of the container is shown and is applied to a similarly modified cover arrangement. In this shape, the container includes a central body portion 50 with a pair of wings 51 and 52. The compartments extend longitudinally of the central body portion that is at right angles to the extent of the wings. The length of the compartments in the wings is very much less than the length of the compartments in the central body portion.

The cover 53 is similarly shaped so that each half of the cover will overlie or underlie the container 50 to prevent direct contact of the container with the skin of the user. This shape is particularly effective for use around the neck of the user and the base of the head and the base of the neck because the central body portion is applied to the rear of the neck and the wings are wrapped around to the sides and the front of the neck.

Various other sizes and designs can be made to fit any region of the body, with both the sand container section and the cover being suitably shaped for cooperation with the body part.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A therapy pad comprising a substantially planar container having two sides, a filler material received within the container, the container being formed from a flexible fabric material which is resistant to heating and freezing, is permeable to moisture and retains the filler material within the container, the container being formed into a plurality of separate elongate parallel tubular compartments each extending substantially wholly across a width of the sides of the container and the compartments being arranged in a row from one end of the sides of the container to an opposed end of the container with each compartment being separated from a next to allow flexing of the container about a line between the compartments, the filler material consisting substantially wholly of sand, and a cover for the container separate from the container and comprising a padded fabric body shaped to cover both sides of the container, the cover comprising a first side for engaging over and covering one of said sides of the container and a second side for engaging over and covering the other of said sides of the container, each of the sides of the cover having a shape and dimension substantially equal to that of the container, and the sides of the cover being connected along one common side edge such that the cover can be folded along said one common side edge, allowing the first and second sides to be opened into a flat panel and folded to an overlying condition to receive the container therebetween, the cover including fastening means for holding the first and second sides in the folded overlying condition, the cover being formed of a first layer of fabric, a first layer of padding attached to said first layer of fabric, a second layer of fabric, a second layer of padding attached to said second layer of fabric, said first layer of fabric and said first layer of padding being attached to said second layer of fabric and said second layer of padding with the first and second layers of padding facing inwardly toward each other, said first side only of the cover having within said padded fabric body thereof between said first and second layers of padding a layer substantially coextensive with said container which is impermeable to moisture and said second side being permeable to moisture.

* * * * *